US011724022B2

(12) United States Patent
Langseth-Manrique et al.

(10) Patent No.: US 11,724,022 B2
(45) Date of Patent: Aug. 15, 2023

(54) TAILORED DOSE OF CONTRAST AGENT

(71) Applicant: GE HEALTHCARE AS, Oslo (NO)

(72) Inventors: Karina Martha Langseth-Manrique, Oslo (NO); Duncan Wynn, Buckinghamshire (GB)

(73) Assignee: GE HEALTHCARE AS, Oslo (NO)

( * ) Notice: Subject to any disclaimer, the term of this patent is extended or adjusted under 35 U.S.C. 154(b) by 532 days.

(21) Appl. No.: 16/956,925

(22) PCT Filed: Dec. 20, 2018

(86) PCT No.: PCT/EP2018/086359
§ 371 (c)(1),
(2) Date: Jun. 22, 2020

(87) PCT Pub. No.: WO2019/122223
PCT Pub. Date: Jun. 27, 2019

(65) Prior Publication Data
US 2020/0390965 A1    Dec. 17, 2020

(30) Foreign Application Priority Data

Dec. 20, 2017  (GB) ..................................... 1721463

(51) Int. Cl.
| | | |
|---|---|---|
| *A61M 5/00* | (2006.01) | |
| *A61K 49/04* | (2006.01) | |
| *A61K 49/10* | (2006.01) | |
| *A61M 5/315* | (2006.01) | |
| *B65B 3/00* | (2006.01) | |
| *B65B 13/00* | (2006.01) | |

(52) U.S. Cl.
CPC ......... *A61M 5/007* (2013.01); *A61K 49/0438* (2013.01); *A61K 49/0476* (2013.01); *A61K 49/103* (2013.01); *A61K 49/106* (2013.01); *A61M 5/31546* (2013.01); *B65B 3/00* (2013.01); *B65B 3/003* (2013.01); *B65B 13/00* (2013.01); *A61M 2205/52* (2013.01); *A61M 2205/6072* (2013.01)

(58) Field of Classification Search
CPC ...... A61M 5/31546; B65B 3/00; B65B 3/003; B65B 13/00
See application file for complete search history.

(56) References Cited

U.S. PATENT DOCUMENTS

| | | | |
|---|---|---|---|
| 5,450,847 A | 9/1995 | Kampfe et al. | |
| 5,911,252 A * | 6/1999 | Cassel | B65B 3/003 604/407 |
| 6,506,155 B2 * | 1/2003 | Sluis | A61B 8/00 600/437 |
| 2004/0051368 A1 * | 3/2004 | Caputo | G16H 40/40 299/1.9 |
| 2004/0199076 A1 | 10/2004 | Nemoto | |
| 2007/0255135 A1 | 11/2007 | Kalafut et al. | |
| 2009/0198208 A1 | 8/2009 | Stavsky et al. | |
| 2011/0207824 A1 * | 8/2011 | Douleau | A61K 47/12 53/469 |
| 2011/0208047 A1 | 8/2011 | Fago | |
| 2014/0319005 A1 * | 10/2014 | Jachwitz | B65B 3/003 53/425 |
| 2015/0238160 A1 | 8/2015 | Flohr et al. | |
| 2020/0390965 A1 * | 12/2020 | Langseth-Manrique | B65B 3/26 |

FOREIGN PATENT DOCUMENTS

| | | |
|---|---|---|
| CA | 2077712 C | 6/2003 |
| CN | 1533812 A | 10/2004 |
| CN | 102202705 A | 9/2011 |
| CN | 102512186 A | 6/2012 |
| CN | 104856717 A | 8/2015 |
| EP | 1016427 A2 | 7/2000 |
| JP | H069435 A | 1/1994 |
| JP | H09503419 A | 4/1997 |
| JP | 2008500119 A | 1/2008 |
| JP | 2009268823 A | 11/2009 |
| JP | 2012232029 A | 11/2012 |
| JP | 2013220184 A | 10/2013 |
| WO | 9511722 A1 | 5/1995 |
| WO | 0103757 A2 | 1/2001 |

OTHER PUBLICATIONS

German Search Report received in Application No. GB1721463.6, dated May 17, 2018, 5 pages.
Notification of Transmittal of the International Search Report and the Written Opinion of the International Searching Authority, or the Declaration, International Application No. PCT/EP2018/086359, dated Apr. 2, 2019, 14 pages.
Office Action received in Chinese Application No. 201880082303.9 dated Sep. 3, 2021, with translation, 23 pages.
Yuijie, et al., "Complicated Issues on Interventional Cardiology" Contrast Media, China Peking Union Medical University Press, Dec. 2005, with translation, 26 pages.
Office Action received in Japanese Application No. 2020-534260 dated Sep. 6, 2022, with translation, 8 pages.
Second Office Action received in Japanese Application No. 2020-534260 dated Sep. 6, 2022, with translation, 8 pages.

* cited by examiner

*Primary Examiner* — Timothy L Maust
(74) *Attorney, Agent, or Firm* — Jeff B. Vockrodt; Culhane Meadows, PLLC

(57) ABSTRACT

Disclosed herein are novel procedures, systems and excipient solutions for in situ provision of a contrast media at a user defined concentrations. An automated procedure according to embodiments of the current invention provides increased user safety, flexibility and user friendliness.

17 Claims, No Drawings

TAILORED DOSE OF CONTRAST AGENT

TECHNICAL FIELD OF THE INVENTION

The present invention is directed to a method for the facile preparation of tailored individual doses of contrast media.

DESCRIPTION OF RELATED ART

All diagnostic imaging is based on the achievement of different signal levels from different structures within the body so that these structures can be seen. Thus, for a given body structure to be visible in the image, the signal derived from that structure must differ from that of the surrounding tissues. The difference in signal between the body structure and its surroundings is frequently termed contrast and much effort has been devoted to enhancing contrast in diagnostic imaging since the greater the contrast or definition between a body structure or region of interest and its surroundings the higher the quality of the images and the greater their value to the physician performing the diagnosis.

A widely-used approach for improving the diagnostic quality factor has been to introduce contrast enhancing materials formulated as contrast media into the body region being imaged. For the last 50 years the field of X-ray contrast agents has been dominated by soluble iodine containing compounds. Commercial available contrast media (CM) containing iodinated contrast agents are usually classified as ionic monomers such as diatrizoate (Gastrografen™), ionic dimers such as ioxaglate (Hexabrix™), nonionic monomers such as iohexol (Omnipaque™), iopamidol (Isovue™), iomeprol (Iomeron™) and the nonionic dimer iodixanol (Visipaque™). The clinical safety of iodinated X-ray contrast media has continuously been improved over the recent decades through development of new agents; from ionic monomers (Isopaque) to non-ionic monomers (e.g. Omnipaque) and non-ionic dimers (e.g. Visipaque™). However, even the highly refined X-ray contrast media currently on the market exhibit a low degree of undesirable clinical side effects, such as Contrast Induced Nephropathy (CIN), adverse cardiac events, and delayed adverse reactions (DARs). Consequently, there is a clinical need for a new and safer X-ray contrast medium, especially in connection with diagnostic investigations involving patients where there is a high risk of side effects. A typical characteristic of X-ray contrast media has been high iodine content, frequently measured in milligrams iodine per milliliter, such as 270-400 mg I/ml. However, to reduce the risk of adverse events, especially in susceptible subjects, to improve patient safety and to reduce costs, there is now a desire to reduce the amount of X-ray contrast media administered to patients undergoing X-ray examinations. At the same time, there is a need for providing contrast media of higher iodine concentrations when needed. Thus, it is desirable that the contrast agent concentration and injection volume can be adjusted based on the individual patient. Factors that affect the right concentration and injection volume for any patient may depend on, for example, the type of examination, age, weight or physical health of the patient.

U.S. Pat. No. 5,840,026, discloses devices and methods to customize the injection to the patient using patient specific data derived before or during an injection. Although differences in dosing requirements for medical imaging procedures based upon patient differences have been recognized, conventional medical imaging procedures continue to use pre-set doses or standard delivery protocols for injecting contrast media during medical imaging procedures.

USRE45717E1 discloses methods to tailor contrast agent concentration for the patient undergoing injection/infusion with an injector system where a powered injector can be used. The desired concentration is obtained by mixing at least two fluid sources.

U.S. Pat. No. 5,592,940A teaches how to make a number of volumes and concentrations available for the patient. A process is described where the contents of a first container with a contrast agent concentrate (in the form of a solution, dispersion or free-flowing powder) and a second container with a diluent are mixed in a chamber.

There remains a need for further improved methods for preparation of patient-tailored doses of contrast agents.

SUMMARY OF THE INVENTION

In one aspect the present invention relates to an automated system for the production of a patient-tailored dose of a contrast agent wherein said system comprises:
  (i) one or more sealed containers containing constituents for the preparation of said contrast agent in a dilutable form and wherein each of said one or more containers comprises an information carrier providing data relating to said constituents;
  (ii) a receiving device for receiving said one or more containers;
  (iii) means to bring a diluent and the constituents of said one or more containers together to result in diluted constituents;
  (iv) means to convey said diluted constituents into a product container;
  (v) means for receiving data wherein said data comprises said data relating to said constituents and patient-specific data; and,
  (vi) software instructions to calculate the amounts of each constituent required for said dose and to direct the preparation of said dose.

In another aspect the present invention relates to a method for the production of a patient-tailored dose of a contrast agent as defined herein wherein said method comprises using the system as defined herein and said method comprises the following steps:
  (a) providing data to said means for receiving data wherein said data comprises data relating to the constituents of said one or more sealed containers and patient-specific data; and,
  (b) applying software instructions to said data to calculate the amounts of each constituent required for said patient-tailored dose and to direct said automated system to prepare said dose.

DETAILED DESCRIPTION OF THE PREFERRED EMBODIMENTS

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "patient-tailored dose" means a particular concentration and volume of contrast agent calculated based upon the type of examination, age, weight or physical health of the patient in question.

A "contrast agent", also often referred to as a contrast medium, is a substance used to enhance the contrast of structures or fluids within the body in medical imaging. In the context of the present invention suitable contrast agents include X-ray contrast agents and magnetic resonance imaging (MRI) contrast agents.

"Sealed containers" can be understood in the context of the present invention to encompass any container suitable for containing one or more constituents for the preparation of the contrast agent. A suitable container controls possible migration of packaging components into the pharmaceutical formulation, controls degradation of the contents, e.g. by oxygen, moisture, heat, etc., prevents microbial contamination and ensures sterility of the contents. Suitable containers when the dilutable form is in solid or powder form can have a volume ranging from 10 mL to 5000 mL. Suitable containers when the dilutable form is in solid or powder form can have a smaller volume, for example ranging from 10 mL to 100 mL and in certain embodiments can be understood to be capsules. A "capsule" herein can be understood according to its mechanical meaning, i.e. a volume contained by a suitable sterile barrier. The volume is typically a sphere, endcapped cylinder or end capped conical cylinder of suitable material, typically metal or polymer or a combination of both.

A "dilutable form" in the context of the present invention can be taken to mean either a solid (e.g. powder) or a concentrated liquid, which in each case can be readily diluted with a diluent within an automated system.

An "information carrier" can be understood herein to refer to any form of machine-readable information attached to each of said one or more capsules. Non-limiting examples of suitable technologies include electronic tags, barcodes and radio-frequency identification (RFID).

"Data relating to said constituents" includes any information relating to the physical properties of the constituents, e.g. chemical and physical identity, quantity, concentration, etc.

A "receiving device" in the context of the present invention is a repository into which the one or more sealed containers can fit securely permitting precise extraction of the constituents therein for dilution.

The "means for bring" the diluent and constituents together and the "means to convey" the diluted constituents into a product container may each comprise a fluid-tight, sterile conduit such as a length of tubing.

The "product container" is any suitable sterile vessel into which the final product is collected and preferably from which administration to the patient is facilitated. Non-limiting examples of product collection containers include vials, syringes, tubing, etc.

A "diluent" is a pharmaceutically-acceptable liquid in which the constituents can readily dissolve.

The term "dissolve" takes its ordinary meaning, i.e. with reference to the present invention for the constituents to become incorporated into the diluent so as to form a solution.

A "means to convey" is a fluid-tight sterile pathway through which the diluted contents can pass without altering their physical and chemical properties. For example, a length of tubing made from medical-grade plastic, which may be a flexible plastic.

A "means for receiving data" is an electronic memory of a computing device, e.g. a computer, tablet or smartphone.

The term "patient-specific data" comprises any data relevant to the health and clinical management of a patient. Non-limiting examples of patient-specific data include body weight, age, gender, radiation dose, type of exam, pregnancy status, allergies and genetics.

"Software instructions" are executable computer code and in the context of the present invention represent instructions that direct the system of the present invention to prepare a dose of contrast agent at a particular concentration, volume and relative concentration of constituents based on the patient-specific data.

An "injector system" is an apparatus designed for the safe and effective administration of a contrast agent. Non-limiting examples of commercially-available injector systems include Peristaltic systems (from Ulrich and Swiss Medical) and Piston systems (from Medirad, Libel Flarsheim, Nemoto).

In one embodiment of the automated system of the invention said contrast agent is an X-ray contrast agent or a magnetic resonance imaging (MRI) contrast agent.

In one embodiment of the automated system of the invention said constituents comprise the API of said contrast agent.

In one embodiment of the automated system of the invention said constituents comprise one or more excipients.

In one embodiment of the automated system of the invention said excipients comprise one or more of a buffer, a chelator and one or more salts.

In one embodiment of the automated system of the invention said constituents comprise a diluent.

In one embodiment of the automated system of the invention one or more sealed containers comprise a first container containing an API of said contrast agent, a second container containing one or more excipients and a third container containing a diluent. For example, for the preparation of the approved formulations of Omnipaque™, the first container may contain iohexol concentrate, the second container may contain TRIS/EDTA mixture and the third container may contain water. The table below illustrates the amounts of each required to obtain different presentations of Omnipaque™.

| Presentation | Tris (10 mM) | Edetate Calcium Disodium (0.27 mM) | Iohexol |
| --- | --- | --- | --- |
| Omnipaque ™ 180 | 121 mg | 10 mg | 38.8 g |
| Omnipaque ™ 240 | 121 mg | 10 mg | 51.7 g |
| Omnipaque ™ 300 | 121 mg | 10 mg | 64.7 g |
| Omnipaque ™ 350 | 121 mg | 10 mg | 75.4 g |

The same principles as illustrated above for Omnipaque™ can be readily applied by those of skill in the art to obtain other commercially-available contrast agents.

In some embodiments of the present invention the contrast agent is prepared in situ, i.e. close to or even right next to the patient. It is further provided in some embodiments that the automated system of the invention is directly linked to and in fluid communication with an injector system such that the contrast agent is prepared and injected into the patient in one continuous process. In these embodiments it is preferred that the constituents of the contrast agent are mixed in tubing attached to the injector system. Once mixed, the contrast agent can be injected directly without use of syringe, and without need to transfer the contrast agent to any other container outside the fluidly connected automated system and injector system. Furthermore, in the context of these embodiments, the present invention provides that some excipients required for commercially-approved contrast agents may not be needed. For example, excipients present in known contrast agent formulations for the purpose of extending shelf-life. Therefore, the contrast agent being used immediately after its preparation has no "shelf life" to speak of. As such simplified formulations can be envisaged, e.g. comprising the API of the contrast agent and a diluent only.

In one embodiment of the automated system of the invention said diluent is selected from water for injection, Sodium Chloride Injection, Ringer's Injection, Dextrose Injection, Dextrose and Sodium Chloride Injection, Lactated Ringer's Injection. In one embodiment said diluent is one well-known to those of skill in the art, for example as taught in Remington's Pharmaceutical Sciences, $22^{nd}$ Edition (2006 Lippincott Williams & Wilkins) and The National Formulary (https://books.google.pl/books?id=O3qixPEMwssC&q=THE+NATIONAL+FOR MULARY&dg=THE+NATIONAL+ FORMULARY&hl=en&sa=X&redir_esc=y).

In one embodiment of the automated system of the invention said contrast agent is an X-ray contrast agent. In one embodiment of the automated system of the invention said X-ray contrast agent is an iodinated x-ray contrast agent. In one embodiment of the automated system of the invention the active pharmaceutical ingredient (API) of said iodinated x-ray contrast agent is a 2,4,6-triiodinated-benzene ring. In one embodiment of the automated system of the invention said 2,4,6-triiodinated-benzene ring is a monomeric 2,4,6-triiodinated-benzene ring. In one embodiment of the automated system of the invention said 2,4,6-triiodinated-benzene ring is a dimeric 2,4,6-triiodinated-benzene ring.

In one embodiment of the automated system of the invention said contrast agent is an MRI contrast agent. In one embodiment of the automated system of the invention the API of said MRI contrast agent is a metal chelate comprising a cheland or a derivative thereof and a paramagnetic metal ion. In one embodiment of the automated system of the invention said paramagnetic metal ion is an ion of a metal of atomic number 21 to 29, 42, 44 and 57 to 71. In one embodiment of the automated system of the invention said paramagnetic metal ion is an ion of a metal of atomic number 57 to 71. In one embodiment of the automated system of the invention said paramagnetic metal ion is selected from Cr, V, Mn, Fe, Co, Pr, Nd, Eu, Gd, Tb, Dy, Ho, Er, Tm, Yb and Lu. In one embodiment of the automated system of the invention said paramagnetic metal ion is selected from Cr(III), Cr(II), V(II), Mn(III), Mn(II), Fe(III), Fe(II), Co(II), Gd(III), Tb(III), Dy(III), Ho(III), Er(III), Tm(III) and Yb(III). In one embodiment of the automated system of the invention said chelate is an acyclic or cyclic polyaminocarboxylate. In one embodiment of the automated system of the invention said chelate is one of DTPA, DTPA-BMA, DOTA and DO3A as described e.g. in U.S. Pat. No. 4,647,447 and WO86/02841.

In one embodiment of the automated system of the invention said container is a capsule.

In one embodiment of the automated system of the invention said constituents are in solid form.

In one embodiment of the automated system of the invention said container is a bottle.

In one embodiment of the automated system of the invention said information carrier is an electronic tag, a barcode, an RFID tag, a QR code, or an optically-readable code.

In one embodiment of the automated system of the invention said system is fluidly connected to an injector system for the administration of the patient-tailored dose to a patient.

In certain embodiments, the volume V2 of contrast to be delivered to the patient can, for example, be calculated based at least in part on a patient parameter. The patient parameter can, for example, be weight, body mass index, body surface area or cardiac output. In one embodiment, the volume V2 is determined by the formula V2=weight*Z, wherein Z is a constant.

In certain embodiments, the required volume of constituents volume of diluent can, for example, be determined by determination of initial parameters of the injection procedure at least in part on the basis of at least one parameter of the patient and a determined scan duration. The at least one parameter of the patient can, for example, be weight, body mass index, body surface area or cardiac output.

The person skilled in the art will be aware of suitable relative amounts of constituents for X-ray contrast agents. For example, the teachings of WO 91/13636 and WO 90/11094 are directed to X-ray contrast agents and to the constituents of their formulations including different salts. There are also numerous studies concerning formulations of X-ray contrast agents with the inclusion of salts. A study by Chai et al. (Acta. Radiol. 2004, 11, 583-593) demonstrates that a formulation of iodixanol containing 19 mM NaCl and 0.3 mM $CaCl_2$ exhibits a lower frequency of ventricular fibrillation than iodixanol alone.

The selection of a counter ion for sodium ion and calcium ion in the aqueous, excipient solution preferably follows the counter ion used in the X-ray contrast media. In a preferred embodiment, the sodium salt is sodium chloride and the calcium salt is calcium chloride. In certain embodiments, the excipient solution further comprises an ingredient that protects the contrast agent from degradation. In a preferred embodiment, the ingredient is a pH controlling agent. The pH controlling agent may be a pH buffer. An exemplary pH controlling agent is Tris (tromethamol, THAM). In another preferred embodiment, the ingredient is a chelating agent. An exemplary chelating agent is EDTA (Calcium sodium edetate). In more preferred embodiments, the excipient solution comprises both a pH controlling agent and a chelating agent is EDTA.

In certain embodiments, the contrast agent may be diluted using an aqueous, excipient solution, over a large iodine concentration, while maintaining isotonicity. WO 2014/158965A1 describes an aqueous, excipient solution, which solution comprises a sodium ion and a calcium ion, wherein said excipient solution is suitable for diluting a diagnostic composition comprising a contrast agent. Such an excipient solution comprises all the constituents required for preparation of the contrast agent apart from the API. Thus, with an aqueous, excipient solution of a proper salt combination, a concentrated contrast agent solution may be diluted to any desired iodine concentration for patient administration. The isotonicity of the solution is maintained throughout the concentration range. The term "isotonicity" used herein to describe a solution means the solution is isotonic with human blood plasma if no net water migration takes place over the blood cell membranes after mixing the solution with human blood. This means that the measured osmolality of the solution is equal to that of human blood plasma (approx. 290 mOsmol/kg water). This is the goal for any parenteral drug formulation, being more important if injection volumes are relatively large (typically >10 ml) and if injection rate is fast.

In certain embodiments the excipients for a patient-tailored dose of an X-ray contrast agent are selected from Tris (Trometamol): e.g. 10 mmol/l or 1.21 mg/ml, NaCa-EDTA: e.g. 0.27 mmol/l or 0.10 mg/ml; NaCl e.g. 119 mmol/l or 6.95 mg/ml; $CaCl_2$ e.g. 1.03 mmol/l or 0.151 mg/ml.

The API of an X-ray contrast agent is typically present at a concentration of between about 70-350 mg l/ml.

Known X-ray contrast agents provided in powder form such as iohexol and iodixanol are highly soluble in water. However, particles can tend to form large, cohesive, sticky aggregates and these dissolve very slowly so that complete dissolution requires extended stirring or elevated temperatures. The automated system of the present invention therefore in certain embodiments also comprises means to facilitate dissolution of the constituents of the contrast agent. For example, these means may comprise one or more of means for heating, for stirring, or to provide ultrasound waves to the mixture of constituents and diluent. In alternative embodiments, the constituents when provided in solid form are provided in a form that can more readily completely dissolve. For example, WO2015133651 A1 relates to the concept of a powdered form of iohexol, describing the characteristics of the powder, and in particular the relatively short times for dissolving in water.

The present invention provides improvements to the known methods for making doses of X-ray contrast agents. However, the person skilled in the art will recognise that the technology can be equally applied for the facile preparation of other contrast agents, e.g. magnetic resonance imaging (MRI) contrast agents.

Non-limiting examples of suitable pharmaceutically-acceptable excipients for MRI contrast agents include buffering agents, stabilizers, antioxidants, osmolality adjusting agents, pH adjusting agents, excess cheland and weak complexes of physiologically tolerable ions. These and other suitable excipients will be well known to those of skill in the art and are further described in e.g. WO1990003804, EP0463644-A, EP0258616-A and U.S. Pat. No. 5,876,695 the content of which are incorporated herein by reference. A non-limiting example of a suitable buffering agent is tromethamine hydrochloride. The excess cheland is any compound capable of scavenging free paramagnetic ion, but not paramagnetic ion retained within the complexes of this invention, as described in EP2988756A1. Although small amounts are essential to human health, overexposure to free paramagnetic ions may result in adverse reactions. The fundamental issue for paramagnetic metal ions is chelation stability. Chelation stability is an important property that reflects the potential release of free metal ions in vivo. It is known that there is a correlation between the amount of excess cheland in a paramagnetic chelate formulation and the amount of paramagnetic metal deposited in animal models (Sieber 2008 J Mag Res Imaging; 27(5): 955-62). Therefore, in another embodiment, an amount of excess cheland is selected that can act as a paramagnetic ion scavenger to reduce or prevent release from the patient-tailored dose post injection. The optimal amount of free cheland will result in the patient-tailored dose having suitable physicochemical properties (i.e. viscosity, solubility and osmolality) and avoiding toxological effects such as zinc depletion in the case of too much free cheland. U.S. Pat. No. 5,876,695 describes in particular an excess of linear chelate, in particular of free DTPA, and this is a non-limiting example of an excess cheland suitable for use as a constituent in the patient-tailored dose of the present invention. WO2009103744 describes a similar formulation strategy, based on the addition of a precise amount of free chelate, to have a very small excess of said chelate and a zero concentration of free lanthanide. The physiologically tolerable ion may in one embodiment be selected from physiologically tolerable ions include calcium or sodium salts such as calcium chloride, calcium ascorbate, calcium gluconate or calcium lactate.

For the purpose of preparing a contrast agent solution, it is important that the blending process is performed under sterile condition and the solutions are made of pharmaceutical grade components. The system for the in situ dilution of a contrast agent also requires a software and algorithm to steer the mixing of the excipient solution and the concentrated contrast agent solution. The software also ensures mixing homogeneity and sterility. Software and algorithms suitable for these applications are well-known.

The patient-tailored dose is in a form suitable for parenteral administration, for example injection and may therefore be formulated for administration using physiologically acceptable excipients in a manner fully within the skill of the art.

Parenterally administrable forms should be sterile and free from physiologically unacceptable agents and should have low osmolality to minimize irritation or other adverse effects upon administration and thus the pharmaceutical composition should be isotonic or slightly hypertonic.

For the pharmaceutical composition of the invention to be administered parenterally, i.e. by injection its preparation further comprises steps including removal of organic solvent. For parenteral administration, steps to ensure that the pharmaceutical composition is sterile and apyrogenic also need to be taken.

Where the container is a capsule it is envisaged that the automated system is a "capsule extraction device" similar to those known in the field of beverage preparation as described for example in WO2005004683 A1. Such devices are designed to be simple, inexpensive and mechanically reliable, thereby providing convenience in the production of a contrast agent. Insertion of a capsule is facilitated in particular to permit insertion and positioning a capsule in an extraction device without trial and error or excessive handling and without risk of bad positioning of the capsule in said device. Application of this technology to the field of contrast agent preparation is completely new and offers potential advantages. Each capsule can contain a particular constituent or more than one constituent, e.g. in the form of an excipient mix as described above.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. An automated system for the production of a patient-tailored dose of a contrast agent close to or next to a patient wherein said system comprises:
   (i) one or more sealed containers comprising constituents for the preparation of said contrast agent in a dilutable form and wherein each of said one or more sealed containers comprises an information carrier providing data relating to said constituents and wherein said one or more sealed containers comprise a first container containing an API of said contrast agent, a second container containing one or more excipients and a third container containing a diluent;
   (ii) a receiving device for receiving said one or more sealed containers;
   (iii) a conduit for bringing the constituents of said one or more sealed containers together to result in diluted constituents;
   (iv) a conduit for conveying said diluted constituents into a product sealed container;
   (v) an electronic memory of a computing device for receiving data wherein said data comprises said data relating to said constituents and patient-specific data; and,
   (vi) software instructions to calculate the amounts of each constituent required for said dose and to direct the preparation of said dose based on said data relating to said constituents and said patient-specific data.

2. The automated system as defined in claim 1 wherein said contrast agent is an X-ray contrast agent or a magnetic resonance imaging (MRI) contrast agent.

3. The automated system as defined in claim 1 wherein said contrast agent is an X-ray contrast agent.

4. The automated system as defined in claim 3 wherein said X-ray contrast agent is an iodinated x-ray contrast agent.

5. The automated system as defined in claim 4 wherein the active pharmaceutical ingredient (API) of said iodinated x-ray contrast agent is a 2,4,6-triiodinated-benzene ring.

6. The automated system as defined in claim 5 wherein said 2,4,6-triiodinated-benzene ring is a monomeric 2,4,6-triiodinated-benzene ring.

7. The automated system as defined in claim 5 wherein said 2,4,6-triiodinated-benzene ring is a dimeric 2,4,6-triiodinated-benzene ring.

8. The automated system as defined in claim 1 wherein said contrast agent is an MRI contrast agent.

9. The automated system as defined in claim 8 wherein the API of said MRI contrast agent is a metal chelate comprising a cheland or a derivative thereof and a paramagnetic metal ion.

10. The automated system as defined in claim 9 wherein said paramagnetic metal ion is an ion of a metal of atomic number 21 to 29, 42, 44 and 57 to 71.

11. The automated system as defined in claim 9 wherein said paramagnetic metal ion is selected from Cr, V, Mn, Fe, Co, Pr, Nd, Eu, Gd, Tb, Dy, Ho, Er, Tm, Yb and Lu.

12. The automated system as defined in claim 9 wherein said chelate is an acyclic or cyclic polyaminocarboxylate.

13. The automated system as defined in claim 12 wherein said chelate is one of DTPA, DTPA-BMA, DOTA and DO3A.

14. The automated system as defined in claim 1 wherein said sealed container is a capsule.

15. The automated system as defined in claim 1 wherein said information carrier is an electronic tag, a barcode, an RFID tag, a QR code, or an optically-readable code.

16. The automated system as defined in claim 1 wherein said system is fluidly connected to an injector system for the administration of the patient-tailored dose to a patient.

17. A method for the production of a patient-tailored dose of a contrast agent wherein said method comprises using the system as defined in claim 1 and said method comprises the following steps:
   (a) providing data to said electronic memory of the computing device wherein said data comprises data relating to the constituents of said one or more sealed containers and patient-specific data; and,
   (b) applying software instructions to said data to calculate the amounts of each constituent required for said patient-tailored dose and to direct said automated system to prepare said dose.

* * * * *